April 13, 1971 J. D. NORTON Plant Pat. 3,040
APPLE TREE
Filed Feb. 24, 1969 3 Sheets-Sheet 1
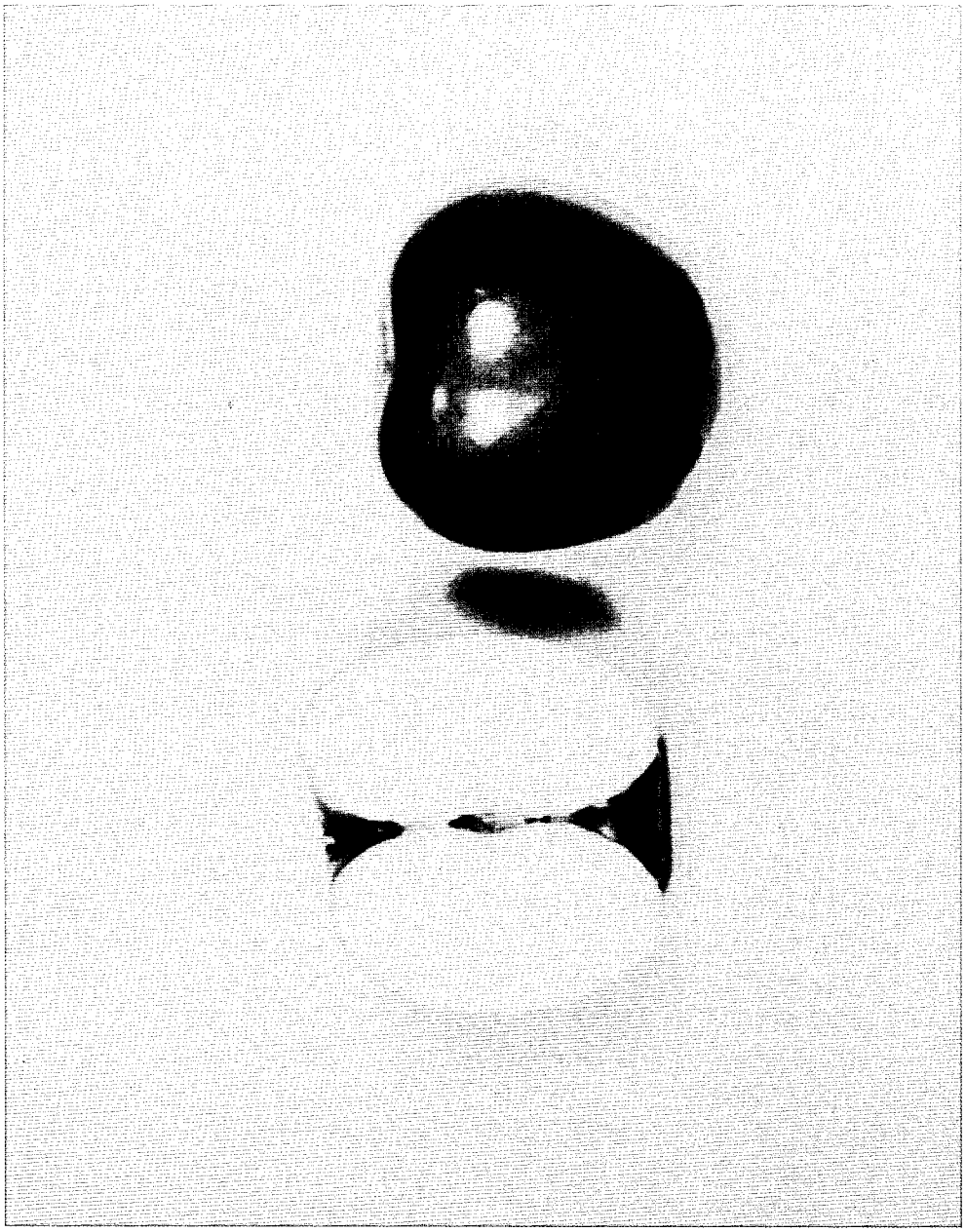
Inventor
Joseph D. Norton
Burns, Doane, Benedict, Swecker & Mathis
Attorneys APPLE TREE
Filed Feb. 24, 1969 3 Sheets-Sheet 2
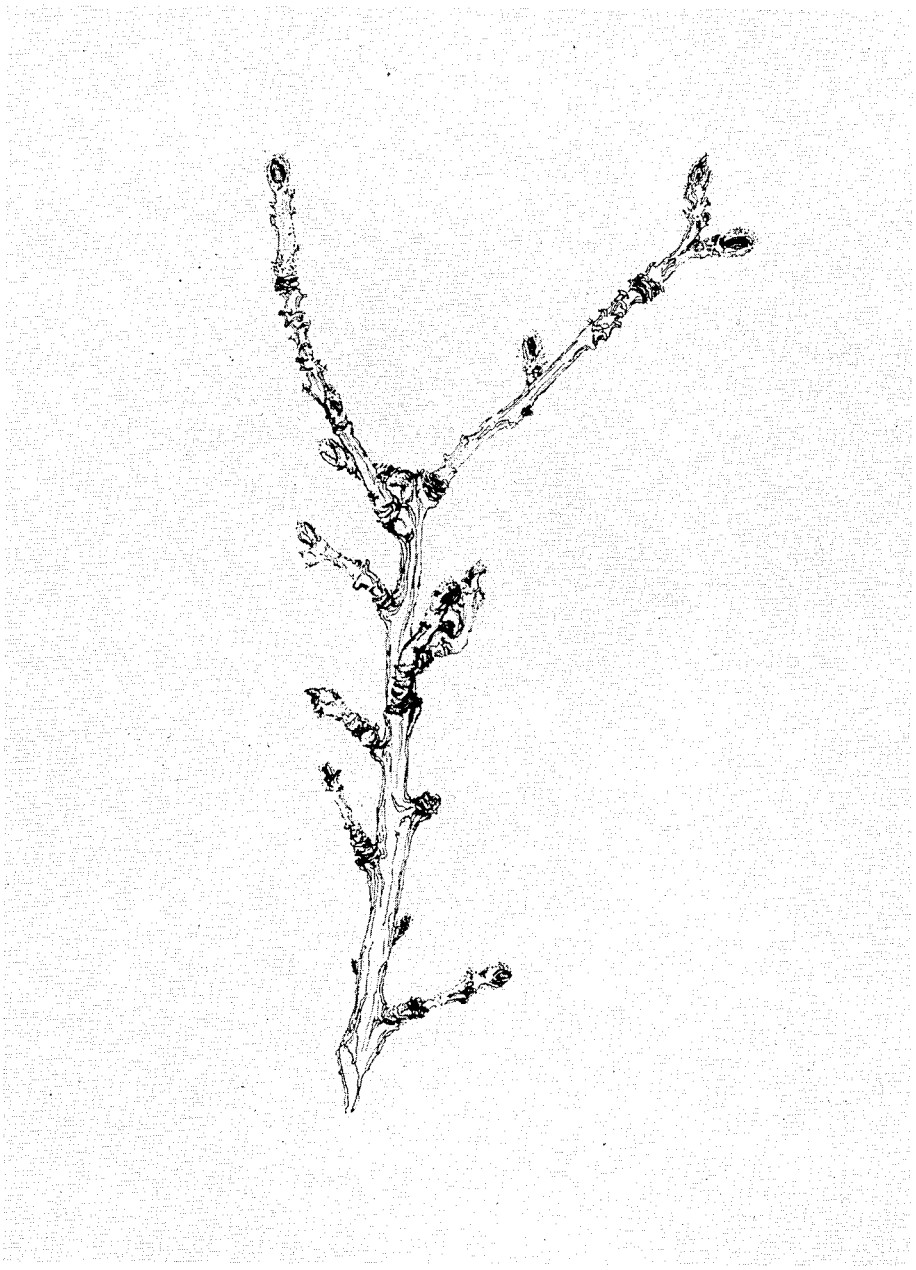
INVENTOR.
JOSEPH D. NORTON,
Barnes, Isaacs, Benedict, Sturdevant & Mathis
BY
ATTORNEYS APPLE TREE
Filed Feb. 24, 1969 3 Sheets-Sheet 3
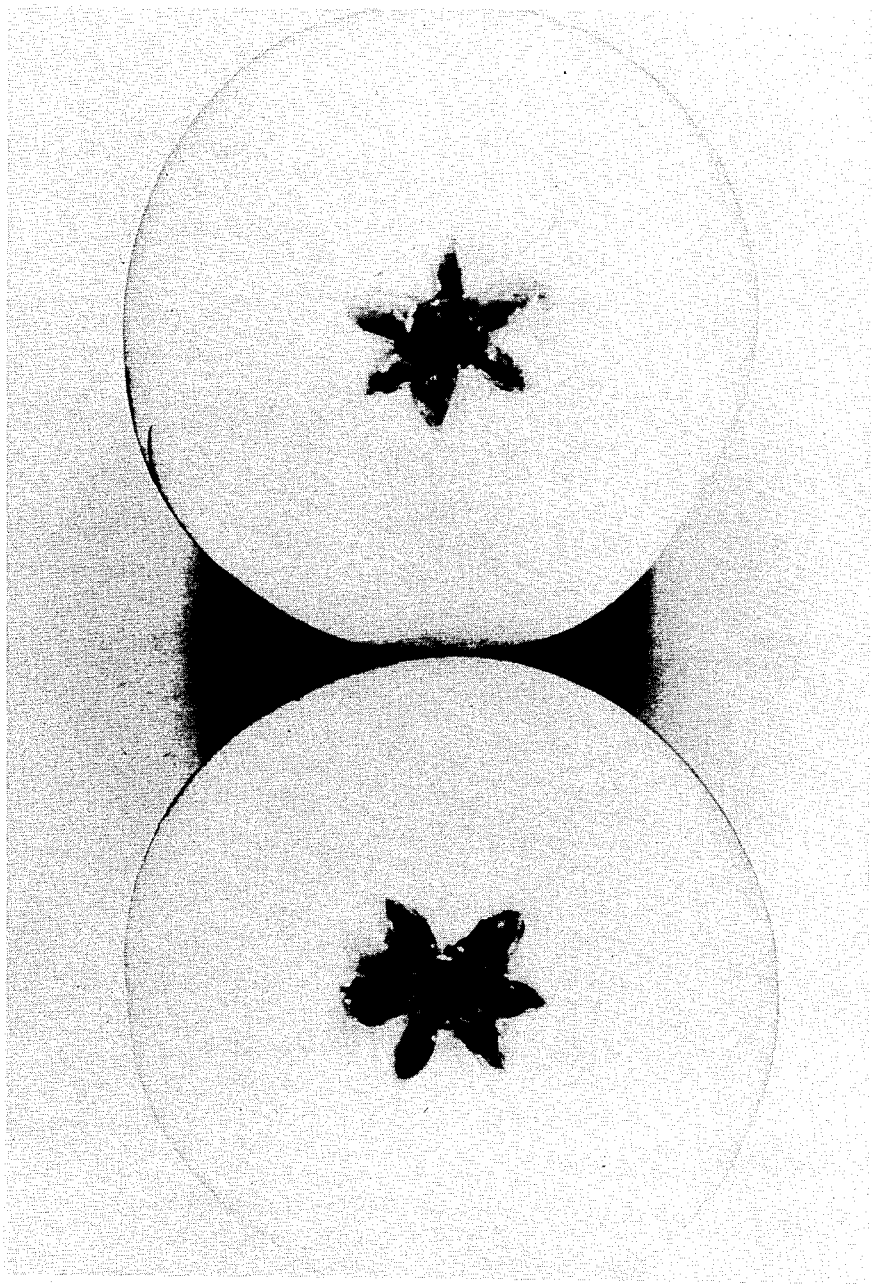
Inventor:
Joseph D. Norton
Brown, Jason, Berenbaum, Sunderland & Mathis
Attorneys

United States Patent Office

Plant Pat. 3,040
Patented Apr. 13, 1971

3,040
APPLE TREE

Joseph D. Norton, 1120 Loftin Drive, Auburn, Ala. 36830

Filed Feb. 24, 1969, Ser. No. 801,871
Int. Cl. A01h *5/03*
U.S. Cl. Plt.—35 1 Claim

ABSTRACT OF THE DISCLOSURE

An apple tree which was discovered by a bud sport as a limb mutation of the variety Vance Red Delicious. In contrast with its parent, the new variety is of the spur type and the fruit is borne on spurs along the branches and ripens earlier, from two to three weeks earlier, than Vance Red Delicious.

BRIEF DESCRIPTION OF THE NEW VARIETY

The present new and distinct variety of apple tree was originally discovered as a sport of the variety Vance Red Delicious, at Auburn, Ala. Trees were budded from the sport and planted at Auburn and at Flat Rock, Ala., and the fruit grown thereon has been observed and compared with its parent.

Tree: Tree is semidwarf, abundant spurs, a moderately vigorous grower. Form roundish or spreading, somewhat drooping with sub-acute angles of branching. Bark of trunk and older branches mostly light gray splotched over light reddish brown. Lenticels sparse on young branches; bark has weakly grayish glaucous covering on light reddish brown. Twigs stout with numerous thick spurs; stipules not prominent, inconspicuous to absent.

Resistance to diseases is comparable to that of the Vance Red variety including a high level of resistance to the Fire Blight organism.

Vegetative buds sparse, small and very lightly pubescent. Leaf glabrous, margin medium dentate serration. Leaf tip acute accuminate. Occasionally elliptical, distinctly inequilateral base, midrib prominent, glabrous or slightly pubescent. Leaf scars prominent, lens shaped. Upper leaf surface grayish green 1 GY 3/2. (Nickerson color fan, maximum chroma, 40 hues, Nickerson Color Company, Inc.) Lower leaf surface moderate olive green 2.5 GY 4/3. Mature leaf length 3½ to 4 inches, leaf width 1¾ to 2 inches.

Flower: Flower buds large with red scales, pink flowers appear about Apr. 10, at Auburn, Ala.

Fruit exterior: Form oblong inclined to conic, the apex oblique and somewhat ribbed. Color strong red 5 F 4/12 at Auburn, Ala., and dark red 5 R 3/7 at Flat Rock, Ala. The fruit averages approximately 3¼ inches in axial dimension and approximately 3 inches in transverse dimension. Skin thin, moderately tough, pale yellow 7.5 F 9/4 overlaid with above reds. Lenticels numerous, small, dark center with yellow halo. Calyx tube funnel shaped, stamens basal. Basin moderately deep, conic, symmetrical. Ripens July 15, Aug. 1, at Auburn, Ala.

Fruit interior: Core open, medium size, abaxial, cells open, core lines clasping. Typically 6 locules instead of 5 with 2 seeds per locule. Endocarp typical, moderate yellow green 2.5 GY 5/5. Accessory tissue tinged with pale yellow 7.5 R 9/4 firm, moderately fine, somewhat crisp, tender, moderately juicy, sweet, excellent delicious flavor.

The accompanying drawings comprises a color photograph of the fruit of the new variety, together with a photograph showing the seed locules in cross section and an illustration of a branch showing the spur characteristics.

The fruit is very beautiful, of a brilliant red color, highly flavored for a dessert apple. The fruit is slightly larger than Vance Red Delicious. The fruit is borne on spurs along the branches, which allows the tree to support a heavy crop of fruit. Thus, it will hold more fruit before damage from weight results. It is earlier ripening, from two to three weeks before Vance Red Delicious. The fruit has six seed locules whereas Vance Red Delicious has five, or fewer. It is resistant to fire blight disease. The leaf is offset or inequal at the base of the leaf blade. It is recommended for general commercial and home garden planting, to be ready for market before Vance Red Delicious fruit would be ready for harvest.

I claim:

1. A new and distinct variety of apple tree characterized particularly by the earlier maturing of the fruit and by its spur type growth as contrasting with its parent Vance Red Delicious, substantially as shown and described.

No references cited.

ROBERT BAGWILL, Primary Examiner